(12) United States Patent
Weisser et al.

(10) Patent No.: US 11,357,558 B2
(45) Date of Patent: Jun. 14, 2022

(54) DRILL WIRE SLEEVE (71) Applicant: Aesculap AG, Tuttlingen (DE)

(72) Inventors: Daniel Weisser, Villingen-Schwenningen (DE); Fabian Mauthe, Talheim (DE)

(73) Assignee: AESCULAP AG, Tuttlingen (DE)

(*) Notice: Subject to any disclaimer, the term of this patent is extended or adjusted under 35 U.S.C. 154(b) by 346 days.

(21) Appl. No.: 16/638,221

(22) PCT Filed: May 29, 2018

(86) PCT No.: PCT/EP2018/064104
§ 371 (c)(1),
(2) Date: Feb. 11, 2020

(87) PCT Pub. No.: WO2019/042603
PCT Pub. Date: Mar. 7, 2019

(65) Prior Publication Data
US 2020/0360066 A1  Nov. 19, 2020

(30) Foreign Application Priority Data
Aug. 30, 2017  (DE) ............... 10 2017 215 142.0

(51) Int. Cl.
A61B 17/86 (2006.01)
A61B 17/84 (2006.01)
(Continued)

(52) U.S. Cl.
CPC .......... *A61B 17/865* (2013.01); *A61B 17/848* (2013.01); *A61B 17/8897* (2013.01); *A61B 50/30* (2016.02)

(58) Field of Classification Search
CPC ... A61B 17/846; A61B 17/848; A61B 17/865; A61B 17/8897; A61B 50/30
See application file for complete search history.

(56) References Cited

U.S. PATENT DOCUMENTS 8,292,174 B2* 10/2012 Bagozzi ............... A61B 90/94
705/28
10,660,683 B2* 5/2020 Wahl ................ B65D 77/0486
(Continued)

FOREIGN PATENT DOCUMENTS

| CN | 205359661 U | 7/2016 | |
| DE | 3119173 A1 | 12/1982 | |
| DE | 3119173 A1 * | 12/1982 | ........... 17/18 |

OTHER PUBLICATIONS

Interlockmed. "Catalogue 2016" A/V A to Z: An Encyclopedic Dictionary of Media, Entertainment and Other Audiovisual Terms, Apr. 21, 2016, Retrieved from the Internet: https://www.interlockmed.com/media/wysiwyg/pdf/katalog/ZSVA/CSSD_-_Catalogue_2016_low.pdf [retrieved on Aug. 23, 2018], pp. 88-89.

(Continued)

*Primary Examiner* — Larry E Waggle, Jr.
(74) *Attorney, Agent, or Firm* — Culhane Meadows, PLLC; Christopher A. Rothe (57) ABSTRACT A drill wire sleeve includes a tubular oblong sleeve having a length, an internal diameter and an external diameter. The drill wire sleeve has a first axial end cap and a second axial end cap. The first axial end cap and/or the second axial end cap is detachably fastenable without tools on the tubular oblong sleeve using a thread and detachably closes an insertion opening of the tubular oblong sleeve. The first axial end cap and/or the second axial end cap has a non-rotationally symmetrical outer cross section and the tubular oblong sleeve has a plurality of first passages in its lateral surface. The first passages are formed oblong and are inclined at an angle of 25° to 65° in relation to the longitudinal axis of the tubular oblong sleeve, preferably at an angle of 28° to 55°, and more preferably at an angle of 31° to 52°.

11 Claims, 5 Drawing Sheets

(51) Int. Cl.
*A61B 17/88* (2006.01)
*A61B 50/30* (2016.01)

(56) References Cited

U.S. PATENT DOCUMENTS 10,752,405 B2 * 8/2020 Richart .............. B65D 83/0005
2009/0266890 A1 10/2009 Bagozzi et al.
2017/0065794 A1 3/2017 Murphy

OTHER PUBLICATIONS

International Search Report and Written Opinion for International Application No. PCT/EP2018/064104, dated Sep. 13, 2018, 7 pages.

* cited by examiner

DRILL WIRE SLEEVE

CROSS-REFERENCE TO RELATED APPLICATIONS

This application is the United States national phase entry of International Application No. PCT/EP2018/064104, filed May 29, 2018, which claims the benefit of priority of German Application No. 10 2017 215 142.0, filed Aug. 30, 2017. The contents of International Application No. PCT/EP2018/064104 and German Application No. 10 2017 215 142.0 are incorporated by reference herein in their entireties.

FIELD

The present invention relates to a drill wire sleeve, i.e., a storage sleeve for drill wires, also called Kirschner wires or K wires, which enables a sterilization of the drill wires without the removal thereof from the storage sleeve, which protects the drill wires from damage and which enables the user to introduce drill wires comfortably into the bearing sleeve. The K wires can preferably also be cleaned in the drill wire sleeve before the sterilization.

BACKGROUND

Drill wires are used, for example, to position and fix bone segments in relation to one another in the event of a fracture.

The drill wires are used above all in percutaneous operations as guide elements for cannulated pedicle screws. For this purpose, the wire is screwed or inserted through a trocar into the affected piece of bone, wherein the desired depth can be determined via a scale applied to the wire. The correct screw length is also determined by this scale. A cannulated screw is now drawn over the drill wire thus fastened and screwed in the predetermined direction into the pedicle. The wire is subsequently removed again. A drill wire is an oblong, wire-shaped body having a distal drill wire tip and a proximal end. The drill wire tip does not necessarily have to be formed pointed in this case, but rather can also be formed blunt, for example, and can be provided with a certain surface roughness, so that precisely speaking drilling is not performed using such a drill wire tip, but rather grinding. However, a real drill tip can also be provided on the drill wire tip. There are also drill wires having a drill wire tip tapering to a point, so-called trocar tips, which can also be provided with a longitudinal knurl or threaded sections. There are also drill wire tips having lateral flattened areas, having eyes in the drill wire tip, or drill wire tips which simply end rounded. A drill wire typically has a diameter of approximately 0.6 mm to 3.0 mm. The proximal end of the drill wire is typically formed blunt. A drill wire can comprise markings along its longitudinal extension, which indicate intraoperatively to the surgeon how deep the drill wire has already penetrated into the tissue. It is solely relevant for this application that a drill wire has an oblong body and comprises a distal end (the drill wire tip) and a proximal end.

There are various known types of storage unit for drill wires in the prior art. On the one hand, there is a type of organizer box for drill wires, in which a single compartment is provided for each group of drill wires (for example, for various diameters or differently formed tips), into which the corresponding drill wires are inserted. The complete organizer box then has to be inserted into a separate perforated basket for cleaning and for storage, however. This type of drill wire storage has the advantage that the drill wires can be cleaned easily and are removable well from the storage. However, this type of storage has the disadvantage that the drill wires are not well protected, for example, against damage when the storage is removed from the perforated basket. Moreover, this type of drill wire storage unit requires a large amount of space and this space is very limited in particular in the operating room. The company MK Medical sells such storage units on their website mk-medical.com. There are also such storage units in which storage unit and perforated basket are connected to one another. Such a storage unit is disclosed, for example, in the published application CN 205359661 U.

Another type of a drill wire storage unit is shown in the publication US 2017/0065794 A1. This type of storage unit is suitable for particularly long drill wires and has an essentially spiral or helical, closed receptacle space made of plastic, to accommodate a drill wire having multiple turns therein, wherein the individual turns are separated from one another by partition walls. Such a drill wire storage unit is not suitable for the cleaning and sterilization of a drill wire, however.

The so-called drill wire sleeve is still another type of drill wire storage unit. In the drill wire sleeve, a hollow cylinder is closed on one side and is closable on one side, wherein the lateral surface of the hollow cylinder is provided with passages, so that cleaning fluid and sterilization medium can penetrate into the drill wire sleeve and the drill wires can be cleaned and sterilized in the drill wire sleeve. Such a drill wire sleeve can comprise a divided interior, so that various types of drill wires can be stored in a drill wire sleeve without mixing with one another. A plurality of drill wire sleeves with and without division, with round or square cross-section, with one closable end cap or two, with end caps made of plastic or metal, etc., are offered, for example, by Interlock on their website interlockmed.com.

A drill wire sleeve is disclosed in the published application DE 31 19 173 A1, in which an essentially cylindrical body is closed on one end face with a screw cover and the interior tapers in a funnel shape on the other end face and comprises a central opening, which is slightly larger than the cross section of a drill wire. In this manner, a type of drill wire dispenser is created, which functions like a toothpick dispenser. The lateral surface of the cylindrical body is provided with oval passages as flushing openings, which are distributed regularly in the longitudinal and circumferential directions. The axes of the individual oval passages are oriented in the longitudinal direction and tangential direction of the sleeve.

The previously disclosed drill wire sleeves have the disadvantage during usage that the leading end of the drill wire can penetrate into one of the passages, which are provided as flushing openings in the lateral surface of the drill wire sleeve, during the insertion of the drill wire into the drill wire sleeve. The leading end of the drill wire, depending on the insertion angle, then comes into contact with the distal wall of the passage. It is unimportant in this case whether the drill wire is pushed with its drill tip or its proximal end in front into the drill wire sleeve. This penetration of the leading end of the drill wire occurs since the drill wire is never introduced exactly linearly (i.e., exactly parallel to the longitudinal axis of the drill wire sleeve) into the drill wire sleeve. The effect is all the greater the larger the angle α of the introduction of the drill wire into the drill wire sleeve is in relation to the longitudinal axis of the drill wire sleeve. If the angle α is relatively small, the leading end of the drill wire slides automatically over the edge which the wall of the oval opening forms with the inner wall surface of the receptacle space of the drill wire sleeve. If the angle α is very large, it can even be that the drill wire will be pushed through the passage. In practice, however, this is rather improbable, since very large angles α may be easily avoided by the user. In a middle range for the angle α, however, the above-described contact can occur. In such a case, the drill wire cannot be pushed further into the drill wire sleeve. The user firstly has to pull the drill wire somewhat out of the drill wire sleeve again and push the drill wire in again at a smaller angle α. This is annoying to the user and costs time. This can result in unrest and errors in the hectic operating room environment. Damage to the drill wire is also not precluded. For example, the drill wire can fall on the floor when it is pulled out again, from which it cannot be picked up again without the affected person making themselves unsterile. Picking up a drill wire which has fallen on the floor requires either an interruption of the operation to dress the affected person in a sterile manner again, or the drill wire remains on the floor until the ending of the operation and forms a continuous source of accidents, since one can easily slip on a drill wire.

SUMMARY

The object of the present invention is therefore to provide a drill wire sleeve, in which striking of the leading end of a drill wire on the distal wall of a cleaning hole at a typical insertion angle α of a drill wire into a drill wire sleeve is reliably prevented when a drill wire is introduced at an angle into a drill wire sleeve.

A drill wire sleeve according to the present invention comprises a tubular, oblong sleeve having a length L, an internal diameter $d_i$, and an external diameter $d_a$. In addition, the drill wire sleeve has a first axial end cap and a second axial end cap, wherein the first axial end cap and/or the second axial end cap is fastenable using a thread without tools in a detachable manner on the tubular, oblong sleeve. Such a tool-free detachable end cap detachably closes an insertion opening of the tubular, oblong sleeve. In addition, the first axial end cap and/or the second axial end cap has a non-rotationally symmetrical outer cross section. The tubular, oblong sleeve has a plurality of first passages in its lateral surface. These first passages are formed oblong and are arranged inclined at an angle of 25 to 65° in relation to the longitudinal axis of the tubular, oblong sleeve.

The inclined arrangement of oblong first passages in relation to the longitudinal axis of the sleeve causes a particular effect. If a drill wire is introduced into a drill wire sleeve formed in this manner in a middle range of an insertion angle α, it can still occur that the leading end penetrates into one of the first passages. In this case, the leading end of the drill wire also comes into contact with the inner edge of the passage, which is formed in the transition from the wall of the passage with the inner wall surface of the sleeve. However, since this first passage is now formed oblong and is moreover inclined in relation to the longitudinal axis of the sleeve, this inner edge is very highly probably also inclined at the point of the contact with the leading end of the drill wire (exception: the contact takes place exactly at the distal end of this first passage, which is extremely improbable, however). The leading end of the drill wire then slides along this edge. Since this edge partially extends in the circumferential direction of the lateral surface of the drill wire sleeve, however, the angle β between the leading end of the drill wire and the longitudinal axis of the sleeve thus changes, i.e., this angle β becomes smaller the farther the leading end of the drill wire slides along the inner edge of the first passage. This occurs either in that the drill wire is elastically deformed (i.e., β<α), or in that the user who holds the section of the drill wire protruding out of the drill wire sleeve follows this movement (i.e., β=α), which is predetermined by the leading end of the drill wire. If the angle β is sufficiently small, the leading end of the drill wire then suddenly slides easily over the inner edge and the drill wire can be pushed very easily further into the drill wire sleeve. Briefly withdrawing and reinserting the drill wire into the drill wire sleeve can thus be efficiently prevented and the above-described problems can thus be avoided.

The oblong first passages are preferably arranged regularly along the circumference of the oblong sleeve and along its axial extension. For example, 4 first passages are arranged in each case in the circumferential direction and thus form a ring-shaped structure. This structure then repeats in the axial direction of the oblong sleeve with a certain spacing in relation to one another, wherein the structure can also be arranged offset in relation to one another by a defined angle in the circumferential direction of the sleeve.

The oblong first passages are preferably arranged inclined at an angle of 28° to 55° in relation to the longitudinal axis of the sleeve and furthermore preferably at an angle of 31° to 52°. Depending on the material of the drill wire and the drill wire sleeve and also on the embodiment of the inner edge of the first passage (sharp or rounded), the leading end of the drill wire slides along the inner edge differently well. In the case of a drill wire sleeve made of metal, for example, made of implant steel, titanium, or comparable alloys, the angle range of 28° to 55° is advantageous for gentle sliding of the leading end of the drill wire along the inner edge. A larger angle is to be preferred in the case of roughened drill wire tips than in the case of smoothly polished drill wire tips.

The angles of inclination of the oblong first passages are specified in this application as the angles which the longitudinal direction of a first oblong passage assumes with the longitudinal axis of the sleeve in an unwinding of the lateral surface of the sleeve.

The nonround cross section of the first and second end caps are used, on the one hand, to enable tool-free detachment thereof from the sleeve and, on the other hand, such a cross section also prevents the drill wire sleeve from being able to roll and thus also from being able to roll off of the table, on which it is set up in the operating room. For example, an end cap can have the outer shape of a wingnut or a polygonal shape.

According to one advantageous design of the present invention, the first passages each extend in the radial direction of the tubular, oblong sleeve over 20% to 60% of the outer circumference of the sleeve, preferably over 28% to 47%. This means that the first passages extend in an angle range of 72° to 216° and preferably of approximately 100° to 170° along the circumference of the sleeve. It is ensured by these dimensions that the leading end of the drill wire can slide sufficiently far along the inner edge of the first passage to thus decrease the angle β enough that the leading end of the drill wire can slide past the inner edge of the first passage.

In principle, one attempts to provide as many flushing openings as possible which are as large as possible on a drill wire sleeve, at least if it is also conceived as a cleaning and/or sterilization storage unit, i.e., as a storage unit in which the drill wire also remains during the cleaning and/or the sterilization. This enables good flushing of the interior of the drill wire sleeve if necessary and thus good cleaning of the drill wire or the drill wires. It is thus also ensured that sufficient sterilization medium reaches all regions of the drill wire sleeve to ensure the complete sterilization of the drill wires in the drill wire sleeve. On the other hand, a sufficient number of webs has to be maintained between the flushing openings that, on the one hand, the contents—the drill wires here—cannot fall out and, on the other hand, the drill wire sleeve is still sufficiently stable. This is not least dependent on the material of the drill wire sleeve.

According to a further advantageous design of the present invention, the first passages are arranged in a first region of the lateral surface of the tubular, oblong sleeve. The first region is located in this case at a distance of approximately $a_1=2*d_i$ to $b_1=12*d_i$ in the axial direction from an edge of the insertion opening, preferably at a distance of approximately $a_2=2.5*d_i$ to $b_2=10*d_i$. This means that the angle $\alpha$ between the insertion direction of the drill wire and the longitudinal axis of the sleeve can be between approximately ±26.6° (corresponds to $2*d_i$) and approximately ±4.7° (corresponds to $12*d_i$) and preferably between approximately ±21.8° (corresponds to $2.5*d_i$) and approximately ±5.7° (corresponds to $10*d_i$).

The relationship between angle $\alpha$ and the location of the first region is computed according to:

$$\alpha = \tan^{-1}(d_i/x), \text{ wherein } x \text{ is alternately } a_1, a_2, b_1, \text{ or } b_2.$$

However, this does not mean a lower limit for the angle $\alpha$ for the introduction of the drill wire into the drill wire sleeve. This merely states that if the angle $\alpha$ is less than approximately ±4.7° or preferably approximately ±5.7°, the first passages do not have to be inclined in relation to the longitudinal axis of the sleeve to cause the leading end of the drill wire to slide over the inner edges of the passages. The values $a_1$ and/or $a_2$ thus determine the maximum inclination of the insertion direction of the drill wire in relation to the longitudinal axis of the sleeve. The values $b_1$ and/or $b_2$ determine when the angle $\beta$ has become sufficiently small that the leading end of the drill wire slides over the inner edge of the first passage. It is particularly important in this first region that the first passages are provided.

According to a further advantageous design of the present invention, a plurality of second passages is arranged in a second region of the lateral surface of the tubular, oblong sleeve. This second region is located between the edge of the insertion opening and the first region and the second passages are formed essentially circular and have a smaller cross-sectional area than the first passages. It is advantageous if no first passages are provided in this second region directly in the vicinity of the insertion opening of the drill wire sleeve, but rather second passages having small cross section. The drill wire, if the user wishes to insert it into the drill wire sleeve at an angle which is much too large, then cannot be pushed through one of the passages, so that the drill wire nonetheless falls out of the drill wire sleeve. Since an increased rigidity is required in particular in the vicinity of the insertion opening of the drill wire sleeve for screwing the end cap on and off, essentially circular holes having relatively small cross section are advantageous.

According to still a further advantageous design of the present invention, the lateral surface of the tubular, oblong sleeve comprises a third region, which is not a first region or a second region. First passages and/or second passages and/or other passages are provided in this third region. In this region, the precise shape, location, and arrangement of the passages is not important, so that arbitrary passages can be provided here as long as they are sufficient as flushing openings and leave sufficient rigidity to the drill wire sleeve. Sections can also be provided in this third region which do not comprise any passages, for example, to provide inscriptions.

According to another advantageous design of the present invention, the first axial end cap and/or the second axial end cap has a polygonal outer cross section and furthermore preferably a hexagonal outer cross section. A polygonal cross section is easy to produce and enables simple actuation with the hand even if surgical gloves are worn. In particular a hexagonal outer cross section, i.e., a hexagon, is particularly easy to produce. Moreover, a hexagon is still nonround in such a way that a correspondingly formed drill wire sleeve cannot roll and thus also cannot fall off of the table. At the same time, the edges are not so pointed or sharp in the case of a hexagon that a surgical glove is damaged. This can occur more easily in the case of a triangular outer cross section.

BRIEF DESCRIPTION OF THE DRAWING FIGURES

Further advantages and features of the invention are apparent to a person skilled in the art from the appended figures and the detailed description of the exemplary embodiments. In the figures.

DETAILED DESCRIPTION

Figure 1:
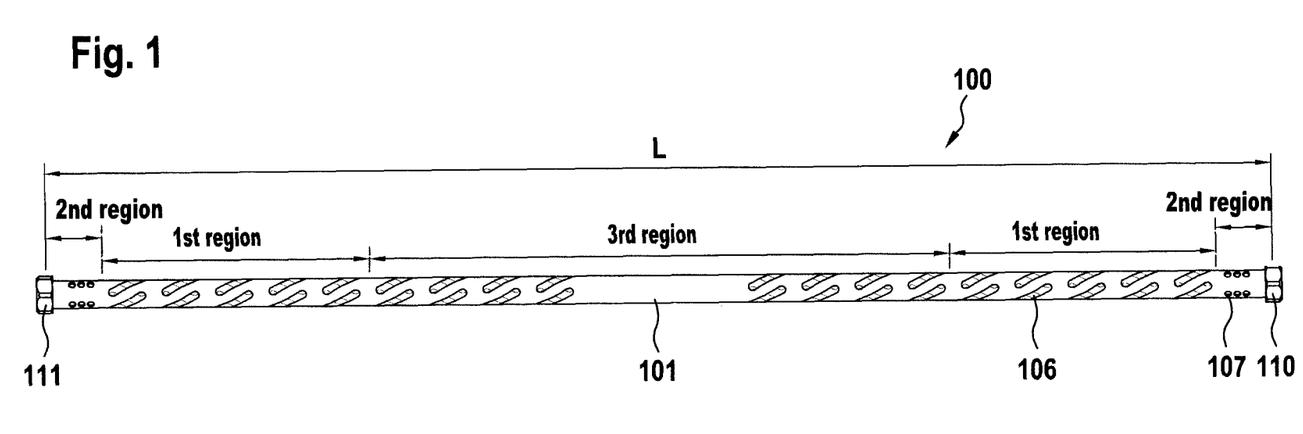
FIG. 1 shows a view of a first exemplary embodiment of the present invention.
Figure 2:
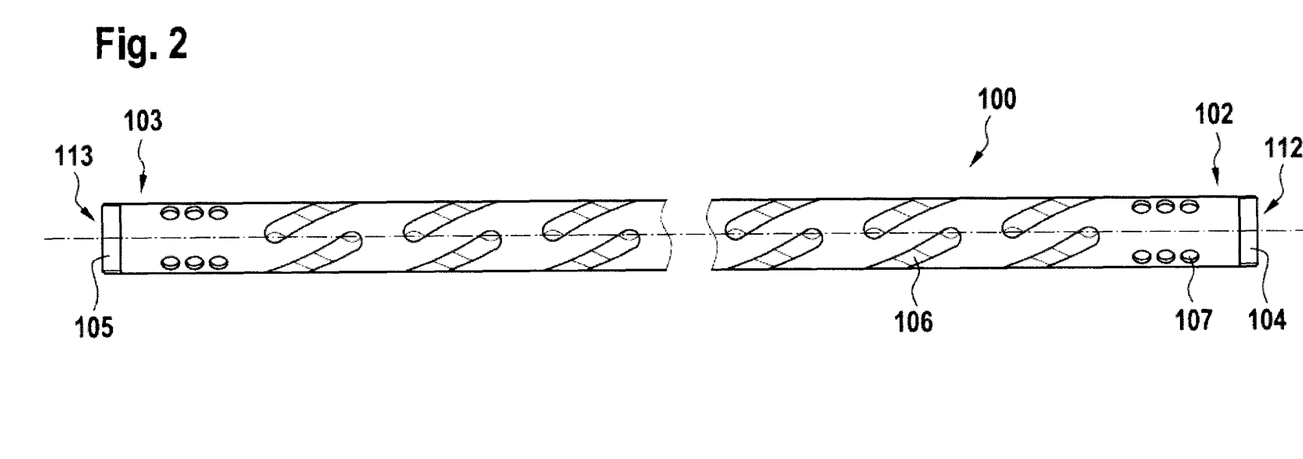
FIG. 2 shows a view of the axial end sections according to the first exemplary embodiment of FIG. 1.

A first exemplary embodiment of the present invention is described hereafter in detail with reference to FIGS. 1 to 3.

A drill wire sleeve 100 is shown in FIG. 1. The drill wire sleeve 100 consists of a tubular, oblong sleeve 101 having a length L of 540 mm, an internal diameter $d_i$ of 10 mm and an external diameter $d_a$ of 12m. A first axial end cap 110 and a second axial end cap 111 are each provided with an internal thread. A first axial end 102 and a second axial end 103 of the sleeve 101 are each provided with an external thread 104 or 105, respectively. The first axial end cap 110 and the second axial end cap 111 can each be screwed onto the threads 104, 105 and unscrewed therefrom without tools using the internal thread thereof and thus detachably close the two axial ends 110, 111 of the sleeve 101 without tools. The threads 104, 105 each have a length of approximately 3 mm. The axial ends 110, 111 can both be used as insertion openings 112, 113 for a drill wire 1 in this exemplary embodiment. Of course, an insertion opening 112, 113 in this application is also always a removal opening, from which a drill wire 1 can be removed from the drill wire sleeve 100. The two end caps 110, 111 each have a hexagon as the external cross section, so that they can also be operated using a corresponding standard tool. A hexagon as the external cross section of the end caps 110, 111 is also particularly advantageous because a hexagon is sufficiently nonround so that the drill wire sleeve 100 does not begin to roll even if it is placed on a non-level surface or if it inadvertently receives a lateral impact. At the same time, the angles in a hexagon are not so acute that a user could injure themselves or damage the sterile glove on a sharp edge. The sleeve 101 of the drill wire sleeve 100 comprises a plurality of oblong first passages 106. These first passages 106 are provided in particular in the two first regions, which are shown in FIG. 1, but also partially in the third region. Circular second passages 107 are provided in the two second regions. In each case 3 of the second passages 107 are arranged equidistantly in the axial direction in each second region, so that they form a row of second passages 107. Four of these rows are arranged uniformly along the circumference of the sleeve 101. The second passages have a diameter of approximately 3 mm and are spaced apart approximately 1 mm in the axial direction. The first passages 106 are formed oblong as already described and arranged inclined at an angle of approximately 26° in relation to the longitudinal axis of the tubular, oblong sleeve 101. The first passages each have a length of approximately 20 mm and a width of approximately 3 mm. Each four of the first passages arranged inclined are provided distributed uniformly along the circumference of the sleeve 101 and thus form a ring of first passages. A plurality of these rings of first passages are arranged in the axial direction of the sleeve 101. A spacing of approximately 4 mm is provided between two such rings of first passages. The first passages extend in this exemplary embodiment over somewhat more than 45° of the circumferential direction of the sleeve 101.

The two first regions each began at a distance of approximately $2.6*d_i$ from the two axial ends 110, 111 of the sleeve, i.e., at a distance of approximately 26 mm, and each extend up to a distance of approximately $10*d_i$ 100 mm from the two axial ends 110, 111 of the sleeve, i.e., up to a distance of approximately 100 mm. In the first region, 5 rings of first passages are provided. Except for the first passages 106, no further passages are provided in the first region and no first passages 106 are provided in the second region.

A third region is provided between the two first regions of the sleeve 101. Further rings of first passages 106 are provided in this region, however, a region is also provided therein in which no passages are present. In this region, inscriptions can be provided, for example, brand name, article number, or items of information relevant to authorization or usage.

Figure 3A:
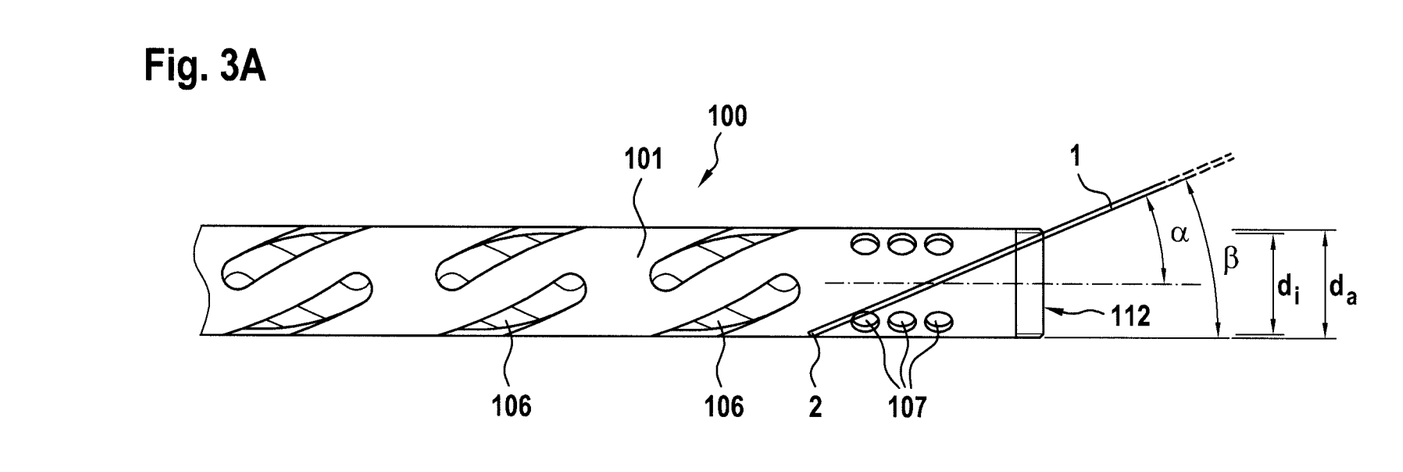
FIG. 3 shows a view of an axial end section according to the first exemplary embodiment of FIG. 1 having a drill wire.
Figure 3B:
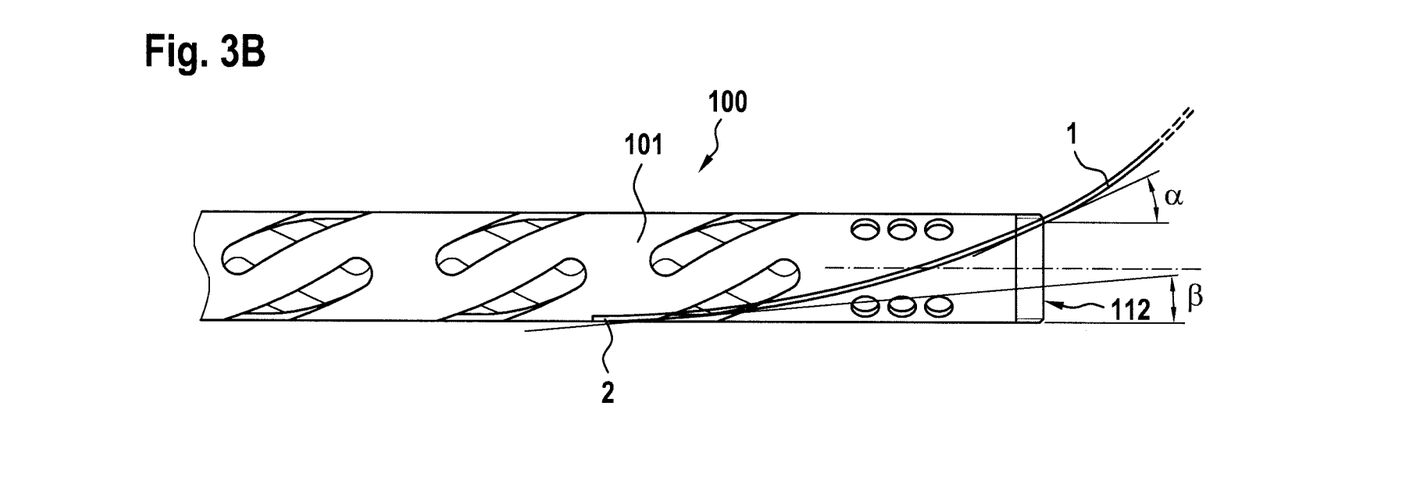

FIGS. 3A and 3B show how a drill wire 1 is inserted into the insertion opening 112 of the sleeve 101 of the drill wire sleeve 100. The drill wire is inserted at an angle α. FIG. 3A shows an extreme example, i.e., an insertion of the drill wire 1 into the sleeve 101 at a very large angle α, which is 22° in this case. The leading end 2 of the drill wire 1 comes into contact on the inner wall surface of the sleeve 101 in this case in the transition region between the second region and the first region of the sleeve 101. The angle β between the leading end 2 of the drill wire 1 and the inner wall surface of the sleeve 101 is initially β=α=22°. If the drill wire 1 is now inserted further into the sleeve 101, there are essentially two possible scenarios. The angle α remains identical and the drill wire 100 is bent during the further insertion or the drill wire 1 remains straight and the angle α is reduced by the person who introduces the drill wire 1 into the sleeve 101. In practice, usually a combination of these two scenarios occurs, i.e., the drill wire is bent and simultaneously the user reduces the angle α slightly. In FIG. 3B, which shows a situation in which the drill wire 1 was inserted further into the sleeve 101, the drill wire is now bent and thus the angle β between the leading end 2 of the drill wire and the inner wall surface of the sleeve 101 is now less than the insertion angle α of the drill wire into the insertion opening 112 of the sleeve 101.

Figure 3C:
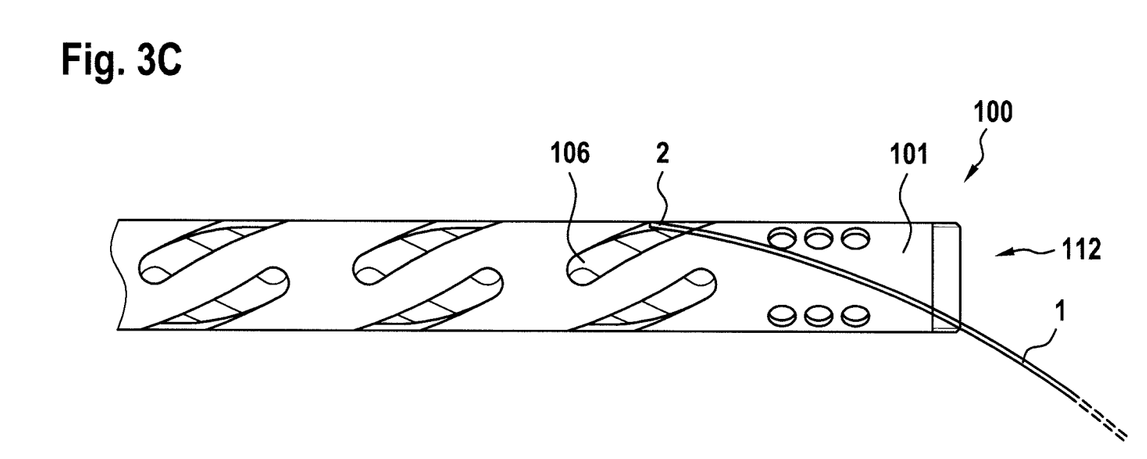
Figure 3D:
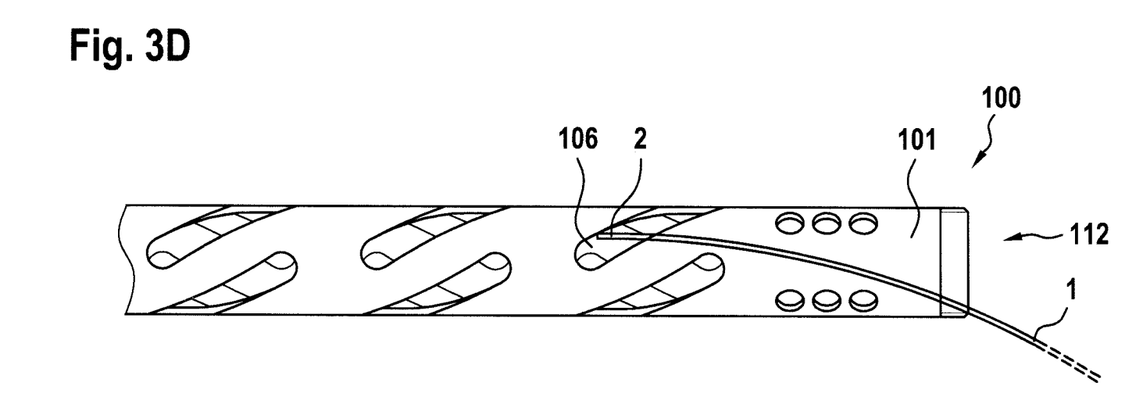

If the leading end 2 of the drill wire 1 now plunges into a first passage 106 during this procedure, as shown in FIG. 3C, the leading end 2 strikes on a longitudinal edge of this passage 106 and slides along it, since it is inclined in relation to the longitudinal axis of the sleeve 101. The leading end 2 of the drill wire 1 is thus moved proportionally in a circumferential direction of the sleeve 101. As shown in FIG. 3D, this effect additionally significantly reduces the angle β and ensures that this angle β becomes sufficiently small that the leading end 2 of the drill wire 1 slides over this longitudinal edge. From the position in FIG. 3C to that in FIG. 3D, the leading end 2 of the drill wire 1 is thus not only moved further to the left in the view of these figures, but rather also in a direction toward the observer. An effect in a third dimension perpendicular to the plane of the illustration of FIGS. 3C and 3D thus results.

The sleeve of this exemplary embodiment is produced from stainless steel (1.4301). The first and second passages 106, 107 were produced by means of laser cutting.

Figure 4:
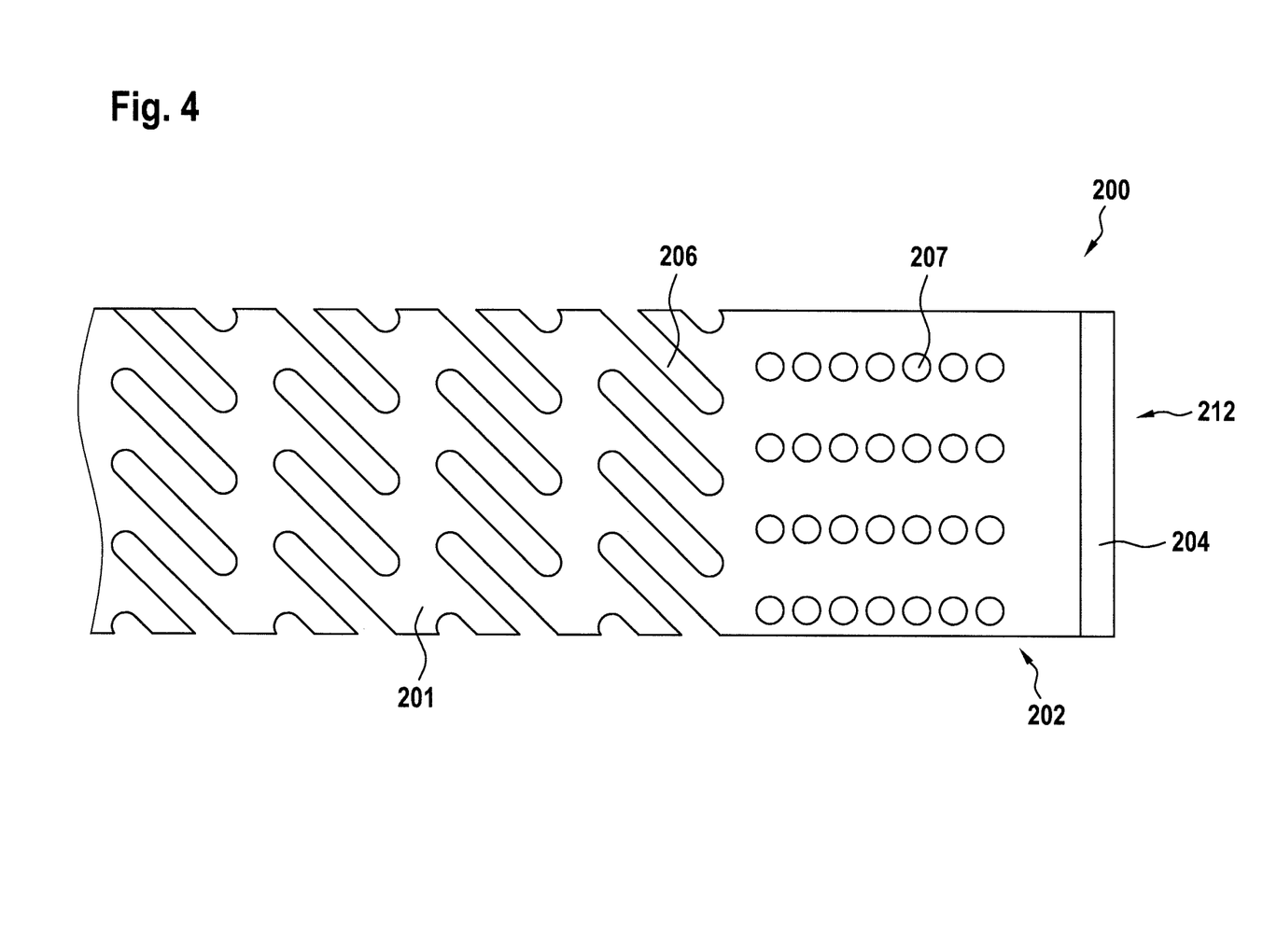
FIG. 4 shows an unwinding of a drill wire sleeve according to a second exemplary embodiment.

An unwinding of an end section of a sleeve 201 of a drill wire sleeve 200 of a second exemplary embodiment is shown in FIG. 4. The fundamental structure of this second exemplary embodiment is identical to that of the first exemplary embodiment. Only the essential differences are described hereafter.

A first axial end 202 of the sleeve 201 comprises an edge of an insertion opening 212, which is provided with an external thread 204, to be detachably closed without tools using a first end cap, which comprises an internal thread corresponding to the external thread 204. The second axial end is permanently closed using a second end cap. In this drill wire sleeve, only one first region, one second region, and one third region is thus formed in each case. The first end cap has a hexagonal outer contour, the second end cap has a square outer contour. The external thread has a length of approximately 5 mm.

The first passages 206 of this exemplary embodiment are approximately 20 mm long, 3 mm wide, and inclined by approximately 51.5° in relation to the longitudinal axis of the sleeve 201. The second passages 207 are circular and have a diameter of approximately 3 mm. In each case 7 of these second passages 207 are arranged in the axial direction of the sleeve 201 in the second region. The first region extends from 42 mm distance to the insertion opening 212 to 120 mm distance to the insertion opening 212 at an internal diameter $d_i$ of the sleeve of 10 mm.

The drill wire sleeve 201 of this exemplary embodiment is manufactured from surgical steel. The first and second passages 206, 207 are produced by means of laser cutting.

Figure 5:
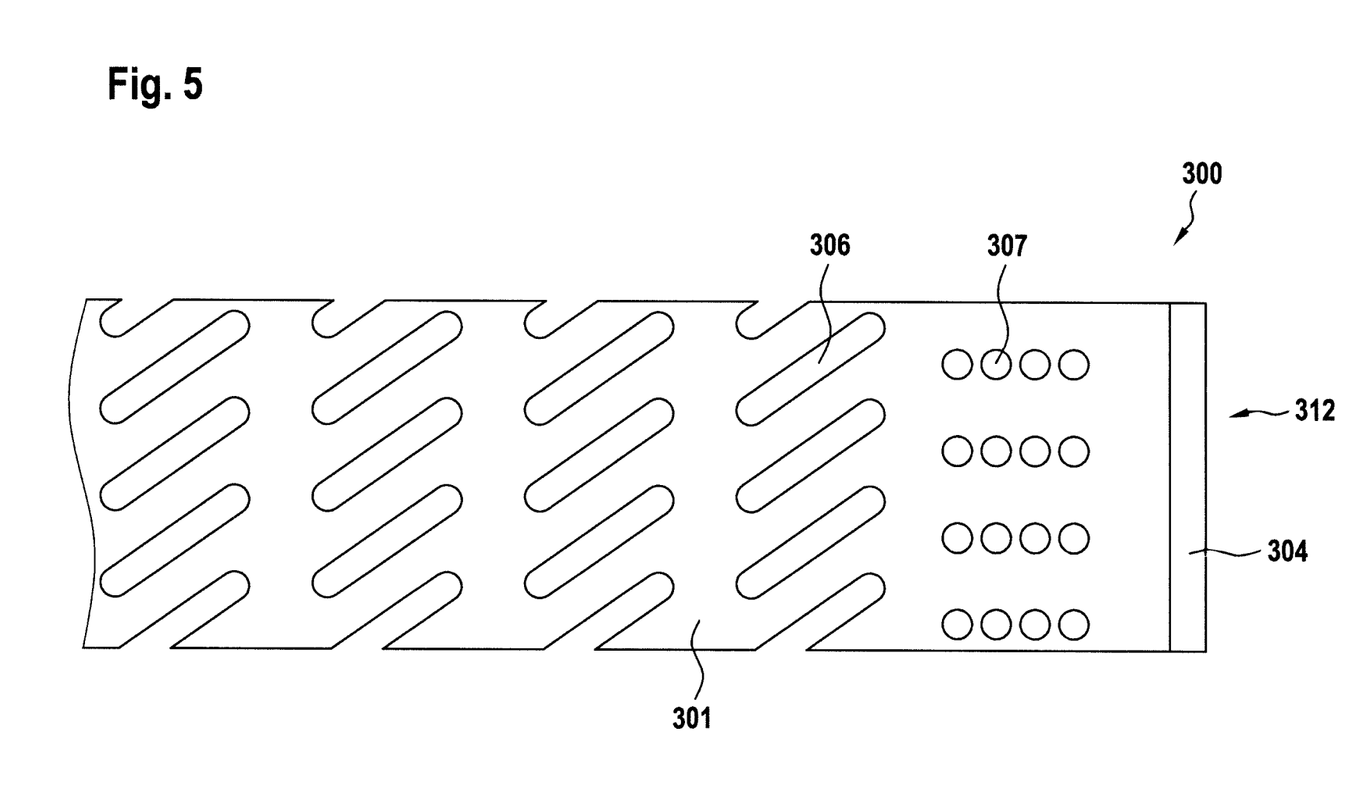
FIG. 5 shows an unwinding of a drill wire sleeve according to a third exemplary embodiment.

A third exemplary embodiment of the present invention is shown in FIG. 5. Again only the differences from the first exemplary embodiment are described hereafter.

The two first regions extend from 20 mm distance to the edge of the insertion opening 312 to 90 mm distance to the edge of the insertion opening 312 at an internal diameter $d_i$ of the sleeve 301 also of 10 mm. The external thread 304 has a length of approximately 4 mm. The first passages 306 have a length of approximately 18.5 mm, a width of approximately 3 mm, and are inclined by approximately 31.5° in relation to the longitudinal axis of the sleeve 301. In each case four second passages 307 are provided in the axial direction of the sleeve 301. The external diameter $d_a$ of the sleeve 301 is 11.5 mm, so that the wall thickness of the sleeve 301 is less than in the first exemplary embodiment.

It is clear to a person skilled in the art that numerous embodiments of the present invention are possible beyond the specific exemplary embodiments. For example, the first passages can be bent or curved in all exemplary embodiments, have a variable width, and the like. The internal diameter can be selected as larger for thicker guide wires or for accommodating a larger number of guide wires. Greatly varying materials come into consideration for producing the drill wire sleeves, for example, cobalt-chromium alloys and also all further metals and alloys which are used in the surgical field and can be re-sterilized.

The second passages can be formed oval or polygonal and more or fewer than four of the second passages can be provided in the circumferential direction of the sleeve. The first passages do not have to be provided in ring-type structures but rather can be arranged offset in relation to one another. More or fewer than four of the first passages distributed in the circumferential direction of the sleeve can also be provided. It is also possible to provide the first and second passages nonuniformly in the axial direction and/or circumferential direction of the sleeve. Moreover, individual features of the various exemplary embodiments can be combined or exchanged with one another suitably.

The invention claimed is:

1. A drill wire sleeve comprising:
   a tubular oblong sleeve having a length L, an internal diameter di, and an external diameter da,
   a first axial end cap; and
   a second axial end cap,
   at least one of the first axial end cap and the second axial end cap is detachably fastenable without tools on the tubular oblong sleeve using a thread and detachably closes an insertion opening of the tubular oblong sleeve,
   at least one of the first axial end cap and the second axial end cap has a non-rotationally symmetrical outer cross section, and
   the tubular oblong sleeve comprises a lateral surface and a plurality of first passages in the lateral surface,
   the first passages are formed oblong and are inclined at an angle of 25° to 65° in relation to a longitudinal axis of the tubular oblong sleeve.

2. The drill wire sleeve according to claim 1, wherein the first passages each extend over 20% to 60% of an outer circumference of the tubular oblong sleeve in a radial direction of the tubular oblong sleeve.

3. The drill wire sleeve according to claim 2, wherein the first passages each extend over 28% to 47% of the outer circumference of the sleeve in the radial direction of the tubular oblong sleeve.

4. The drill wire sleeve according to claim 1, wherein:
   the first passages are arranged in a first region of the lateral surface of the tubular oblong sleeve; and
   the first region is located in a section which is located at a distance of 2*di to 12*di in an axial direction from an edge of the insertion opening.

5. The drill wire sleeve according to claim 4, wherein:
   a plurality of second passages is arranged in a second region of the lateral surface of the tubular oblong sleeve;
   the second region is located between the edge of the insertion opening and the first region; and
   the second passages are substantially circular and have a smaller cross-sectional area than the first passages.

6. The drill wire sleeve according to claim 5, wherein:
   the lateral surface of the tubular oblong sleeve comprises a third region; and
   the first passages, and/or the second passages and/or other passages are in the third region.

7. The drill wire sleeve according to claim 4, wherein the first region is located in a section which is located at a distance of 2.5*di to 10*di in the axial direction from the edge of the insertion opening.

8. The drill wire sleeve according to claim 1, wherein:
   at least one of the first axial end cap and the second axial end cap has a polygonal outer cross section.

9. The drill wire sleeve according to claim 8, wherein the polygonal outer cross section is a hexagonal outer cross section.

10. The drill wire sleeve according to claim 1, wherein the first passages are inclined at an angle of 28° to 55°.

11. The drill wire sleeve according to claim 1, wherein the first passages are inclined at an angle of 31° to 52°.

* * * * *